(12) United States Patent
Chace

(10) Patent No.: US 6,455,321 B1
(45) Date of Patent: Sep. 24, 2002

(54) METHOD FOR INTERPRETING TANDEM MASS SPECTROMETRY DATA FOR CLINICAL DIAGNOSIS

(75) Inventor: Donald H. Chace, Pittsburgh, PA (US)

(73) Assignee: Neo Gen Screening, Inc., Bridgeville, PA (US)

( * ) Notice: Subject to any disclaimer, the term of this patent is extended or adjusted under 35 U.S.C. 154(b) by 0 days.

(21) Appl. No.: 09/464,132

(22) Filed: Dec. 16, 1999

Related U.S. Application Data

(63) Continuation-in-part of application No. 09/277,119, filed on Mar. 26, 1999, now Pat. No. 6,258,605.
(60) Provisional application No. 60/117,880, filed on Jan. 30, 1999.

(51) Int. Cl.[7] .............................................. G01N 24/00
(52) U.S. Cl. .......................... 436/173; 436/86; 702/22; 702/23; 702/27
(58) Field of Search ..................... 436/86, 173; 702/22, 702/23, 27

(56) References Cited

U.S. PATENT DOCUMENTS

| | | |
|---|---|---|
| 5,072,115 A | 12/1991 | Zhou |
| 5,251,126 A | 10/1993 | Kahn et al. |
| 5,365,426 A | 11/1994 | Siegel et al. |
| 5,453,613 A | 8/1995 | Gray et al. |
| 5,545,895 A | 9/1996 | Wright et al. |
| 5,878,746 A | 3/1999 | Lemelson et al. |

OTHER PUBLICATIONS

Shigematsu, Yosuke et al., "Prenatal Diagnosis of Organic Acidemias Based on Amniotic Fluid Levels of Acylcarnitines". Pediatric Research, vol. 39, No. 4, pp. 680–684. (1996) –abstract.*

Nada, Mohamed et al., "Investigation of Beta–Oxidation Intermediates in Normal MCAD–Deficient Human Fibroblasts Using Tandem Mass Spectrometry". Biochemical and Molecular Med., vol. 54, No. 1, pp. 59–66. (1995) –abstract.*

Chace, Donald H., "Used of phenylalanine–to–tyrosine ratio determined by tandem mass spec . . . ", Clin. Chem. 44:12, 1998.

Chace, Donald H. et al., "Rapid Diagnosis of MCAD deficiency: quantitative analysis of octanoylcarnitine . . . ", Clin. Chem., 43:11, 1997.

U.S. patent application Ser. No. 09/277,119, filed Mar. 26, 1999.

* cited by examiner

Primary Examiner—Jill Warden
Assistant Examiner—Monique T. Cole
(74) Attorney, Agent, or Firm—McKay & Associates, PC

(57) ABSTRACT

A method for interpreting data that is produced after a group of amino acids and acylcarnitines are derivatized from blood spots taken from newborn babies and scanned by a tandem mass spectrometer. Concentration levels of each metabolite, which are directly proportional to the butyl ester fragment after derivatization, are compared to threshold flags for determining a significance of any deviation of the metabolite relative to the flag threshold. The threshold flags are diagnostic limits to the data retrieved from each blood spot. The data includes metabolite concentrations and molar ratios of metabolites with other metabolites. Samples are labeled normal for a disease if the concentration of any of the metabolite concentrations or molar ratio concentration do not deviate from the flag threshold, but, in contrast, the sample must be further evaluated if a value is elevated or deficient to some degree. Thus, as each metabolite fragments at a different mass to charge value (m/z), corresponding data is compared to the respective flag thresholds for determining a next course of action that must be taken to ultimately assist a physician in the diagnosis of a genetic disorder resulting from an elevation or deficiency of the metabolite particular for that disorder.

20 Claims, 13 Drawing Sheets

FIG. 4

Propionyl Carnitine (C3) *butyl ester*   m/z 274

*Mean Values:*

| Metabolite | C3 (uM) | C3 mrm (uM) | C3mrm/C2 | C3/C16 |
|---|---|---|---|---|
| Mean Concentration | 1.7 | 1.69 | 0.10 | 0.48 |
| (+) 3 Std. Dev | 3.4 | 3.81 | 0.21 | 1.12 |
| (+) 5 Std. Dev | 4.6 | 5.23 | 0.29 | 1.54 |

*Automated Interpretation Flag Settings:*

| C3 (uM) | C3mrm | C3mrm/C2 | C3/C16 |
|---|---|---|---|
| 5.0 | no flag set | 0.3 | 1.75 |

} 40

*Criteria for Re-Analysis:*
1. Any flag of C3 (5.0 or greater)
2. If both C3/C16 ≥ 1.75 and C3/C2 > 0.3 and C3 > 2.5
3. C3 > 4 and either C3/C16 > 1.75 or C3/C2 > 0.3

} 41

*Criteria for STAT Re-Analysis and Immediate Preliminary Follow-Up*
1. Initial Concentration of C3 > 9
2. Initial Concentration of C3 > 7 and C3/C2 > 0.3 or C3/C16 > 1.75

} 42

*Criteria for Initiating follow-up:*
1. Mean C3 Concentration > 5.5
2. Mean C3 Concentration > 4.0 and either C3/C2 > 0.3 or C3/C16 > 1.75
3. Mean Concentration of C3 > 3.5 and C3/C16 > 1.75 and C3/C2 > 0.3
4. Mean Concentration C3 > 3.5 and either C3/C16 > 1.75 or C3/C2 > 0.3 and age > 5 days

*Follow-Up Recommendations and Interpretation Guide with Codes*

| Code # | Criteria | Interpretation | Follow-Up |
|---|---|---|---|
| C3-001 | C3 > 5.5 | Mild Elevation of Propionylcarnitine | Routine Repeat |
| C3-002 | 4.0 < C3 < 7<br>C3/C2 > 0.3 or C3/C16 > 1.75 | Mild Elevation of Propionylcarnitine | Routine Repeat |
| C3-003 | C3 > 3.0<br>C3/C2 > 0.3 and C3/C16 > 1.75 | Mild Elevation of Propionylcarnitine | Routine Repeat |
| C3-010 | 4.0 < C3 < 7<br>C3/C2 > 0.3 and C3/C16 > 1.75 | Moderate Elevation of Propionylcarnitine. | Urgent Repeat Clin.ical Eval. |
| C3-020 | 7 < C3 < 9 | Moderate Elevation of Propionylcarnitine. | Urgent Repeat Clin. Eval.. |
| C3-100 | 7 < C3 < 9<br>C3/C2 > 0.3 or C3/C16 > 1.75 | Significant Elevation of Propionylcarnitine. | Urgent Repeat, OA, Clin. Eval. |
| C3-200 | C3 > 9 | Significant Elevation of Propionylcarnitine. | Urgent Repeat, OA, Clin. Eval. |

} 43

*Special Notations*

| High Risk: Modifications | | Postmortem Modifications | |
|---|---|---|---|
| Repeat: | C3 > 3.5 uM (blood) 3uM (plasma) | Repeat: | C3 > 6 uM and C3/C2 > 0.3 |
| Follow-Up: | C3 > 3.5 and either C3/C2 or C3/C16 flag | Follow-Up: | C3 > 6 and C3/C2 > 0.3 |
| Interpretation: | Elevated Propionylcarnitine | Interpretation: | Elevated Propionylcarnitine |
| Follow-Up: | Organic Acids (OA), Clinical Evaluation | Follow-Up: | Original Spot, Bile, Clin.. History |

FIG. 5

Isovaleryl Carnitine (C5) *butyl ester*      m/z 302

*Mean Values:*

| Metabolite | C5 (uM) |
|---|---|
| Mean Concentration | 0.18 |
| (+) 3 Std. Dev | 0.38 |
| (+) 5 Std. Dev | 0.51 |

*Automated Interpretation Flag Settings:*

| C5 (uM) |
|---|
| 0.8 |

— 50

*Criteria for Re-Analysis:* — 51
1. Any flag of C5 (0.8 or greater)

*Criteria for STAT Re-Analysis and Immediate Preliminary Follow-Up* } 52
1. Initial Concentration of C5 > 2
2. Initial Concentration of C5 >1 and C3 > 2.5

*Criteria for Initiating follow-up:*
1. Mean C5 Concentration > 1
2. Mean C5 Concentration > 0.8 and C3 > 2
3. Mean Concentration of C5 > 0.8 and low C2 flag

*Follow-Up Recommendations and Interpretation Guide with Codes*

| Code # | Criteria | Interpretation | Follow-Up |
|---|---|---|---|
| C5-001 | C5 > 1 | Mild Elevation of Isovalerylcarnitine | Routine Repeat |
| C5-002 | C5 > 0.8<br>C3 > 2 | Mild Elevation of Isovalerylcarnitine | Routine Repeat |
| C5-010 | C5 > 2 | Moderate Elevation of Isovalerylcarnitine. | Urgent Repeat<br>Clin. Eval. |
| C5-020 | 0.8 < C5 < 1.5<br>C3 > 2.5 | Moderate Elevation of Isovalerylcarnitine. | Urgent Repeat<br>Clin. Eval. |
| C5-100 | C5 > 3 | Significant Elevation of Isovalerylcarnitine. | Urgent Repeat, organic acids, Clin. Eval. |
| C5-200 | C5 > 2<br>C3 > 2.5 | Significant Elevation of Isovalerylcarnitine. | Urgent Repeat, organic acids, Clin. Eval. |

} 53

*Special Notations*

| High Risk: Modifications | Postmortem Modifications |
|---|---|
| Repeat: C5 > 0.75 (plasma)<br>Follow-Up: C5 > 0.8<br>             C5 > 0.75 and low acetyl flag<br>Interpretation: Elevated Isovalerylcarnitine<br>Follow-Up: Organic Acids, Clin. Eval. | Repeat     C5 > 3 uM<br>Follow-Up:   C5 > 3 uM  C4 < 2uM<br>               C5> 5 uM<br>Interpretation: Elevated Isovalerylcarnitine<br>Follow-Up: Original Spot, Bile, Clin. Hist. |

FIG. 6

Methionine (Met)_butyl ester    m/z 206

*Mean Values:*

| Metabolite | Met (uM) | Met/Phe |
|---|---|---|
| Mean Concentration | 17 | 0.33 |
| (+) 3 Std. Dev | 31 | 0.54 |
| (+) 5 Std. Dev | 41 | 0.69 |

*Automated Interpretation Flag Settings:*

| Met (uM) | Met/Phe |
|---|---|
| 60 | 1 |

} 60

*Criteria for Re-Analysis:*
1. Any flag of Met > 60
2. Any flag of Met > 50 and Met/Phe > 1     } 61

*Criteria for STAT Re-Analysis and Immediate Preliminary Follow-Up*
1. Initial Concentration of Met > 150
2. Initial Concentration of Met > 125 and Met/Phe > 1.25     } 62

*Criteria for Initiating follow-up:*
1. Mean Met Concentration > 60
2. Mean Met Concentration > 50 and Met/Phe > 1

*Follow-Up Recommendations and Interpretation Guide with Codes*

| Code # | Criteria | Interpretation | Follow-Up |
|---|---|---|---|
| Met-001 | Met > 60 | Mild Elevation of Methionine | Routine Repeat |
| Met-002 | Met > 50, Met/Phe >1 | Mild Elevation of Methionine | Routine Repeat |
| Met-003 | Met > 60<br>Tyr > 150 | Mild Elevation of Methionine with mild Tyrosine (Liver Function?) | Routine Repeat phone consult |
| Met-010 | Met > 100 | Moderate Elevation of Methionine | Urgent Repeat |
| Met-100 | Met > 150 | Significant Elevation of Methionine | HomoCyst. Referral |
| Met-200 | Met > 125<br>Met/Phe > 1.25 | Significant Elevation of Leucine | HomoCyst. Referral |
| HAL-099 | Met > 80<br>Met/Phe < 1, Leu, Phe elevated | Elevation of Met and other AAs | Hyper-Alimentation Phone Consult |

Glutaryl Carnitine (C5DC, *C10-OH*) *butyl ester*     *m/z* 388

*Mean Values:*

| Metabolite | C5DC (uM) | C5DC:C16 |
|---|---|---|
| Mean Concentration | 0.06 | 0.02 |
| (+) 3 Std. Dev | 0.13 | 0.04 |
| (+) 5 Std. Dev | 0.18 | 0.06 |

*Automated Interpretation Flag Settings:*

| C5-DC (uM) | C5DC:C16 |
|---|---|
| 0.17 | 0.10 |

} 70

*Criteria for Re-Analysis:*
1. Any flag of C5-DC > 0.17 uM
2. C5DC/C16 > 0.12 and C5 > 0.14

} 71

*Criteria for STAT Re-Analysis and Immediate Preliminary Follow-Up*
1. Initial Concentration of C5-DC > 0.4
2. Initial Concentration of C5-DC > 0.2 and C5DC:C16 > 0.2

} 72

Criteria for Initiating follow-up:
1. Mean C5DC Concentration > 0.20 uM
2. Mean C5DC Concentration > 0.15 uM and C5DC:C16 > 0.14
3. Mean C5DC > 0.14 and low C2

*Follow-Up Recommendations and Interpretation Guide with Codes*

| Code # | Criteria | Interpretation | Follow-Up |
|---|---|---|---|
| C5DC-001 | C5DC > 0.2 | Mild Elevation of glutarylcarnitine | Routine Repeat |
| C5DC-002 | C5DC > 0.15<br>C5DC:C16 > 0.14 | Mild Elevation of glutarylcarnitine | Routine Repeat |
| C5DC-010 | C5DC > 0.35 | Moderate Elevation of glutarylcarnitine | Urgent Repeat, Clin. Eval. |
| C5DC-020 | C5DC > 0.2<br>C5DC:C16 > 0.2 | Moderate Elevation of glutarylcarnitine | Urgent Repeat Clin. Eval. |
| C5DC-100 | C5DC > 0.5 | Significant Elevation of glutarylcarnitine | Urgent Repeat, OA, Clin. Eval. |
| C5DC-200 | C5DC > 0.35<br>C5DC:C16 > 0.25 | Significant Elevation of glutarylcarnitine | Urgent Repeat, OA, Clin. Eval. |

} 73

Special Notations

| High Risk: Modifications | Postmortem Modifications |
|---|---|
| Repeat: C5DC > 0.12 uM and C5DC:C16 > 0.10<br>Follow-Up: C5DC > 0.14 uM C5DC:C16 > 0.12<br>Interpretation: Elevated glutarylcarnitine<br>Follow-Up: Organic Acids, Clin. Eval. | Repeat: C5DC > 0.22 uM, C5DC:C16 > 0.25<br>Follow-Up: C5DC > 0.25 uM,<br>    C5DC:C16: > 0.25 uM<br>Interpretation: Elevated glutarylcarnitine<br>Follow-Up: Original Spot, Bile, Clin. History |

FIG. 8

Phenylalanine (Phe) *butyl ester (with Tyr)*     *m/z* 222

*Mean Values:*

| Metabolite | Phe (uM) | Tyr (uM) | Phe/Tyr |
|---|---|---|---|
| Mean Concentration | 53 | 78 | 0.76 |
| (+) 3 Std. Dev | 84 | 167 | 1.5 |
| (+) 5 Std. Dev | 105 | 227 | 2.0 |

*Automated Interpretation Flag Settings:*

| Phe (uM) | Tyr (uM) | Phe/Tyr |
|---|---|---|
| 130 | 350 | 2.5 |

— 80

*Criteria for Re-Analysis:*
1. Any flag of Phe > 130
2. Any flag of Tyr > 350
3. Any flag of Phe/Tyr > 2.5 and Phe > 100

} 81

*Criteria for STAT Re-Analysis and Immediate Preliminary Follow-Up*
1. Initial Concentration of Phe > 240
2. Initial Concentration of Phe > 180 and Phe/Tyr > 2.5

} 82

*Criteria for Initiating follow-up:*
1. Mean Phe Concentration > 180 and Phe/Tyr > 2.0
2. Mean Phe Concentration > 125 and Phe/Tyr > 2.5
3. Mean Phe Concentration > 220 and Phe/Tyr < 2.5 + Leu or Met flags (Hyper-Al verification)
4. Mean Tyr Concentration > 350

*Follow-Up Recommendations and Interpretation Guide with Codes*

| Code # | Criteria | Interpretation | Follow-Up |
|---|---|---|---|
| Phe-001 | Phe > 140<br>P/T > 2.5 | Mild Elevation of Phe | Routine Repeat |
| Phe-002 | Phe > 120<br>P/T > 4 | Mild Elevation of Phe | Routine Repeat |
| Phe-010 | Phe > 180<br>P/T > 2 | Moderate Elevation of Phe | Urgent Repeat |
| HAL-099 | Phe > 220<br>Phe/Tyr < 2.5, Met, Leu flag | Hyper-Alimentation | Card / Phone Consult or Routine Repeat |
| Phe-100 | Phe > 240, P/T > 2.5 | Significant Elevation of Phe | repeat / referral |
| Tyr-001 | Tyr > 350 | Moderate Elevation of Tyrosine | Tyrosine letter |
| Tyr-010 | Tyr > 450 | Significant Elevation of Tyrosine | Routine Repeat, letter |
| Tyr-100 | Tyr > 350, Phe > 100 | Elevation of Tyrosine, Mild Phe | Urgent Repeat, letter |

Leucine (Leu) *butyl ester (as Leu-Ile, with Val)*     m/z 188

*Mean Values:*

| Metabolite | Leu+Ile (uM) | Val (uM) | Leu/Phe | Leu/Ala |
|---|---|---|---|---|
| Mean Concentration | 136 | 104 | 2.61 | 0.66 |
| (+) 3 Std. Dev | 229 | 215 | 4.36 | 1.19 |
| (+) 5 Std. Dev | 291 | 288 | 5.53 | 1.54 |

*Automated Interpretation Flag Settings:*

| Leu+Ile (uM) | Val (uM) | Leu/Phe | Leu/Ala |
|---|---|---|---|
| 325 | 300 | 8.0 | 2.25 |

} 90

*Criteria for Re-Analysis:*
1. Any flag of Leu/Ile > 400
2. Any flag of Leu/Ile > 350 and Val > 300
3. Any flag of Leu/Ile > 325 and Leu/Ala > 2.25 or Leu/Phe > 8.0 and Val > 300

} 91

*Criteria for STAT Re-Analysis and Immediate Preliminary Follow-Up*
1. Initial Concentration of Leu/Ile > 500
2. Initial Concentration of Leu/Ile > 400 and Leu/Phe > 8 and Leu/Ala > 2.25

} 92

*Criteria for Initiating follow-up:*
1. Mean Leu/Ile Concentration > 400
2. Mean Leu/Ile > 350 and Val > 300
3. Mean Leu/Ile > 325 and Val > 300 and Leu/Phe > 8 or Leu/Ala > 2.25
4. Mean Val > 400 uM (with no Proline elevation)

*Follow-Up Recommendations and Interpretation Guide with Codes*

| Code # | Criteria | Interpretation | Follow-Up |
|---|---|---|---|
| Leu-001 | Leu/Ile > 400 uM | Mild Elevation of Leucine | Routine Repeat |
| Leu-002 | Val > 400 uM | Mild Valine (no Proline elevation) | Routine Repeat |
| Leu-003 | Leu/Ile > 350 uM | Mild Elevation of Leucine | Routine Repeat |
| Leu-004 | Leu/Ile > 325 uM, Leu/Ala > 2.25 or Leu/Phe > 8 | Mild Elevation of Leucine | Routine Repeat |
| Leu-010 | Leu/Ile > 450 | Moderate Elevation of Leucine | Urgent Repeat, Clin. Eval. |
| Leu-020 | Leu/Ile > 400 Leu/Ala > 2.25 or Leu/Phe > 8 | Moderate Elevation of Leucine | Urgent Repeat, Clin. Eval. |
| Leu-100 | Leu > 550 | Significant Elevation of Leucine | MSUD Referral, Clin. Eval. |
| Leu-200 | Leu > 450 Leu/Ala > 2.25 or Leu/Phe > 8 | Significant Elevation of Leucine | MSUD Referral, Clin. Eval. |
| HAL-099 | Leu > 400 Leu/Phe < 8, Leu/Ala < 2.25 | Elevation of Leu and other AAs | Hyper-Alimentation Phone Consult |

Citrulline (Cit)*butyl ester*        *m/z* 232

*Mean Values:*

| Metabolite | Cit (uM) | Cit (mrm) |
|---|---|---|
| Mean Concentration | 9 | 10 |
| (+) 3 Std. Dev | 19 | 20 |
| (+) 5 Std. Dev | 26 | 26 |

*Automated Interpretation Flag Settings:*    } 100

| Cit (uM) | Cit (mrm) |
|---|---|
| 55 | 55 |

*Criteria for Re-Analysis:*    /101
1. Any flag of Cit > 55 (either mrm or NTL 102 scan)

*Criteria for <u>STAT</u> Re-Analysis and Immediate Preliminary Follow-Up*
1. Initial Concentration of Cit > 100    ↘ 102

*Criteria for Initiating follow-up:*
1. Mean Citrulline Concentration > 55 for both MRM and NTL 102
2. Mean Citrulline Concentration > 70 on either MRM or NTL 102

*Follow-Up Recommendations and Interpretation Guide with Codes*

| Code # | Criteria | Interpretation | Follow-Up |
|---|---|---|---|
| Cit-001 | Cit > 55 uM | Mild Elevation of Citrulline | Routine Repeat |
| Cit-010 | Cit > 85 uM | Moderate Elevation of Citrulline | Urgent Repeat |
| Cit-100 | Cit > 125 | Significant Elevation of Citrulline | Referral, Citrullinemia, ASA |
| HAL-099 | Cit > 55<br>Met, Phe, or Leu elevated | Elevation of Cit and other AAs | Hyper-Alimentation Phone Consult |

Octanoyl Carnitine (C8) butyl ester (with C6, C10, C10:1)   m/z 344

*Mean Values:*

| Metabolite | C8 (uM) | C8/C16 | C6 (uM) | C10:1 (uM) | C10 (uM) |
|---|---|---|---|---|---|
| Mean Concentration | 0.09 | 0.03 | 0.08 | 0.09 | 0.13 |
| (+) 3 Std. Dev | 0.19 | 0.08 | 0.16 | 0.18 | 0.31 |
| (+) 5 Std. Dev | 0.26 | 0.12 | 0.22 | 0.24 | 0.42 |

*Automated Interpretation Flag Settings:*

| C8 (uM) | C8/C16 | C6 (uM) | C10:1 (uM) | C10 (uM) |
|---|---|---|---|---|
| 0.35 | 0.28 | 0.16 | 0.32 | 0.42 |

— 110

*Criteria for Re-Analysis:*
1. Any flag of C8 (0.4 or greater)
2. If C8 > 0.3 and C8/C16 > 0.15
3. C8 > 0.3 and C6 > 0.2, C10:1 > 0.2 and C10 > 0.3 and Low Acetyl Flag   } 111

*Criteria for STAT Re-Analysis and Immediate Preliminary Follow-Up*
1. Initial Concentration of C8 > 1
2. Initial Concentration of C8 > 0.5 and C8/C16 > 0.35 or C6 > 0.3 and C10:1 > 0.3   } 112

*Criteria for Initiating follow-up and required DNA confirmatory testing:*
1. Mean C8 Concentration > 0.4
2. Mean C8 Concentration > 0.35 and either C8/C16 > 0.3 or C6 > 0.3 or C10:1 > 0.3
3. Mean Concentration of C8 > 0.25 and C8/C16 > 0.25 and low C2 flag

*Follow-Up Recommendations and Interpretation Guide with Codes*

| Code # | Criteria | Interpretation | Follow-Up |
|---|---|---|---|
| C8-001 | C8 > 0.4 | Mild Elevation of Octanoylcarnitine | Routine Repeat DNA: (MCAD/GAII?) |
| C8-002 | 0.3 < C8 < 0.5 C8/C16 > 0.2 or C6 > 0.2 | Mild Elevation of Octanoylcarnitine | Routine Repeat DNA: (MCAD/GAII?) |
| C8-010 | 0.5 < C8 < 1 | Moderate Elevation of Octanoylcarnitine. | Urgent Repeat, Clin.. Eval. DNA: (MCAD/GAII?), |
| C8-020 | 0.5 < C8 < 1 C8/C16 > 0.25 and C6 > 0.25 | Moderate Elevation of Octanoylcarnitine. | Urgent Repeat, Clin. Eval. DNA: (MCAD/GAII?) |
| C8-100 | C8 > 1 | Significant Elevation of Octanoylcarnitine. | Urgent Repeat, organic acids, Clin. Eval. |
| C8-200 | C8 > 1 C8/C16 > 0.3 and C6 > 0.3 | Significant Elevation of Octanoylcarnitine. | Urgent Repeat, organic acids, Clin. Eval. |

} 113

*Special Notations*

| High Risk: Modifications | | Postmortem Modifications | |
|---|---|---|---|
| Repeat: | C8 > 0.25 (blood) C8 > 0.15 (plasma) | Repeat: | C8 > 0.5 uM |
| Follow-Up: | C8 > 0.25 and C8/C16 > 0.25 (blood) C8 > 0.2 (plasma) and low acetyl flag | Follow-Up: | C8 > 0.5 uM C6, C10:1, C10 > 0.4 |
| Interpretation: | Elevated Octanoylcarnitine | Interpretation: | Elevated Octanoylcarnitine |
| Follow-Up: | OA, Blood Spot for DNA, Clin Eval. | Follow-Up: | Original Spot, Bile, Clin. Hist. |

FIG. 12

Myristoyl Carnitine (C14) butyl ester (with C14:1)     m/z 428

*Mean Values:*

| Metabolite | C14 (uM) | C14:1 (uM) | C14:1/C16 |
|---|---|---|---|
| Mean Concentration | 0.24 | 0.13 | 0.05 |
| (+) 3 Std. Dev | 0.45 | 0.28 | 0.11 |
| (+) 5 Std. Dev | 0.56 | 0.38 | 0.17 |

*Automated Interpretation Flag Settings:*

| C14 (uM) | C14:1 | C14:1/C16 |
|---|---|---|
| 0.85 | 0.70 | 0.24 |

— 120

Criteria for Re-Analysis:
1. Any flag of C14 > 0.85 or C14:1 > 0.7
2. If C14 > 0.75 or C14:1 > 0.65 and C14:1/C16 > 0.24

} 121

*Criteria for STAT Re-Analysis and Immediate Preliminary Follow-Up*
1. Initial Concentration of C14 > 2.0 or C14:1 > 1.5
2. Initial Concentration of C14 > 1.5 and C14:1 > 1.0 and C14:1/C16 > 0.3

} 122

Criteria for Initiating follow-up:
1. Mean C14 Concentration > 0.9 or C14:1 Concentration > 0.75
2. Mean C14 Concentration > 0.8 uM or mean C14:1 > 0.65 and either C14:1/C16 > 0.3
3. Mean Concentration of C14 > 0.8 uM and C14:1 > 0.65 and low C2 flag

*Follow-Up Recommendations and Interpretation Guide with Codes*

| Code # | Criteria | Interpretation | Follow-Up |
|---|---|---|---|
| C14-001 | C14 > 0.9 only | Mild Elevation of C14 | Routine Repeat |
| C14-002 | C14:1 > 0.7 only | Mild Elevation of C14:1 | Routine Repeat |
| C14-003 | C14 > 0.85 and C14:1 > 0.7 | Mild Elevation of C14,C14:1 | Routine Repeat |
| C14-004 | C14 > 0.8, C14:1 > 0.65 C14:1/C16 > 0.24 | Mild Elevation of C14,C14:1 | Routine Repeat |
| C14-010 | C14 > 1.25 or C14:1 > 1.0 | Moderate Elevation of C14,C14:1 | Urgent Repeat, Clin.. Eval. |
| C14-020 | C14 > 1.25 or C14:1 > 1.0 C14:1/C16 > 0.25 | Moderate Elevation of C14,C14:1 | Urgent Repeat Clin. Eval. |
| C14-100 | C14 > 2.0 or C14:1 > 1.5 | Significant Elevation of C14,C14:1 | Urgent Repeat, OA, Clin. Eval. |
| C14-200 | C14 > 1.5 or C14:1 > 1.25 C14:1/C16 > 0.3 | Significant Elevation of C14,C14:1 | Urgent Repeat, OA Clin. Eval. |

} 123

Special Notations

| High Risk: Modifications | Postmortem Modifications |
|---|---|
| Plasma | |
| Repeat: C14 or C14:1 > 0.3 uM, C14:/C16>0.3 uM | Repeat: C14 or C14:1 > 1 uM C14:1/C16>0-.3 |
| Follow-Up: C14 or C14:1 > 0.3 uM, C14 or C14:1 > 0.25 and low acetyl flag | Follow-Up: C14 or C14:1 > 1 uM C14:1/C16>0-.3 |
| Interpretation: Elevated C14, C14:1 | Interpretation: Elevated C14, C14:1 |
| Follow-Up: OA, Original Spot, Clin. Eval. | Follow-Up: Original Spot, Bile, Clin. Hist |

FIG. 13

Hydroxy-C5 (C5-OH) *butyl ester* *(w C5:1)*    m/z 318

*Mean Values:*

| Metabolite | C5OH (uM) | C5:1 |
|---|---|---|
| Mean Concentration | 0.20 | 0.04 |
| (+) 3 Std. Dev | 0.42 | 0.09 |
| (+) 5 Std. Dev | 0.57 | 0.13 |

*Automated Interpretation Flag Settings:*

| C5OH (uM) | C5:1 |
|---|---|
| 0.85 | 0.35 |

— 130

*Criteria for Re-Analysis:*  ⎱ 131
1. Any flag of C5OH (0.85 or greater)
2. Any flag of C5:1 of 0.35 or greater

*Criteria for STAT Re-Analysis and Immediate Preliminary Follow-Up*  ⎱ 132
1. Initial Concentration of C5OH > 3
2. Initial Concentration of C5:1 > 1

*Criteria for Initiating follow-up:*
1. Mean C5OH Concentration > 1
2. Mean C5OH Concentration > 0.85 and C3 > 4
3. Mean C5:1 Concentration > 0.4
4. Mean C5:1 Concentration > 0.35 and Mean C5OH > 0.8

*Follow-Up Recommendations and Interpretation Guide with Codes*

| Code # | Criteria | Interpretation | Follow-Up |
|---|---|---|---|
| C5OH-001 | C5OH >1 | Mild Elevation of hydroxy C5 | Routine Repeat |
| C5OH-002 | C5:1 > 0.35 | Mild Elevation of tiglylcarnitine | Routine Repeat |
| C5OH-010 | C5OH > 0.8<br>C5:1 > 0.35 | Possible β-ketothiolase deficiency. | Urgent Repeat |
| C5-OH-020 | C5OH > 2 | Moderate Elevation of hydroxy-C5 | Urgent Repeat |
| C5-OH-100 | C5OH > 3 | Significant Elevation of hydroxy-C5 | Urgent Repeat, Clin. Eval.., OA |
| C3-200 | C5OH > 2<br>C5:1 > 0.75 | Moderate Elevations of C5:1 and C5OH. Probable β-ketothiolase. | Urgent Repeat, Clin. Eval., OA |

⎱ 133

Special Notations

| High Risk: Modifications | Postmortem Modifications |
|---|---|
| none | Repeat         C5OH > 4 uM<br>Follow-Up:    C5OH > 4 uM<br><br>Interpretation: Elevated C5OH<br>Follow-Up:    Original Spot, Bile, Clin. Hist. |

METHOD FOR INTERPRETING TANDEM MASS SPECTROMETRY DATA FOR CLINICAL DIAGNOSIS

SPECIFIC REFERENCE

This is a continuation-in-part of application Ser. No. 09/277,119, filed Mar. 26, 1999, now U.S. Pat. No. 6,258,605, which was entitled to priority date so established for provisional application Ser. No. 60/117,880, filed Jan. 30, 1999, the disclosure of which is herein incorporated by reference.

BACKGROUND

1. Field of the Invention

The present invention relates to a method for interpreting data used for clinical diagnostic purposes. In particular, a decision tree is disclosed for interpreting tandem mass spectrometry data relating to the quantification of metabolites used for diagnosing newborn babies.

2. Description of the Related Art

Automated methods for assessing a patient's condition are known. Computerized systems can be integrated to produce data that can be compared to a known result to allow for proper diagnosing. Such data might be produced by a MRI or CAT scanner, which is used to identify components within the human body.

One particular instrument used for identifying components of interest, whether they are of medicinal or chemical interest, is the mass spectrometer. In reference to U.S. Pat. No. 5,453,613, compounds, when introduced to the electrospray tandem mass spectrometer, are ionized and essentially fragmented. Each fragment produces a peak having local maximums that are matched to reference spectra. A compound can be identified by its associated fragments, each having a mass to charge ratio, which is then relative to the concentrations-of each fragment. All of the reference spectra and compound names can then be stored in a library for correlation and determination. Thus, mass/charge ratios can be used to identify components from known spectra stored in a database.

More recently, however, the use of spectrometry has been implemented in the field of clinical diagnosis. See Chace, U.S. application Ser. No. 09/277,119.

Inborn errors of metabolism usually result from defective enzymes or cofactors. Resulting genetic disorders can be diagnosed by the metabolic profiling of amino acids and acylcarnitines taken from blood spots subjected to a sampling protocol and thereafter introduced into an electrospray tandem mass spectrometer. An electrospray tandem mass spectrometer is very sensitive and specific and can detect a broad spectrum of disorders at the genetic level. With proper standards, data produced from the spectrometer includes values for particular metabolites. The metabolites that are of interest in detecting these disorders are, in particular, amino acids and acylcarnitines/carnitines and the derivatives thereof.

The spectra and resulting concentration values of each metabolite, as derived from mass spectrometry, are then compared to thresholds as a means for evaluating the contents of the blood sample. These thresholds determine the appropriate course of action necessary as a follow-up to the spectral analysis.

As seen in Wright et al., U.S. Pat. No. 5,545,895, spectrometry data is applied to a computerized search database for matching each component as a means of identification.

In a clinical diagnostic setting, there must be further methods for evaluation beyond just that of the identification itself. The numbers must be quantified. Newborns can be born with metabolic disorders, which, if not treated within days, can result in death. Thus, after obtaining MS/MS (tandem mass spectrometer) data from blood samples from newborns, generally of the age of less than seven days old, there is a need for efficiently interpreting this data in relation to pre-determined metabolite concentration thresholds. This interpretation allows for proper decision-making necessary for the diagnosing and follow-up testing of newborns.

SUMMARY OF THE INVENTION

The objective of the present invention is to provide a method for interpreting electrospray tandem mass spectrometry data from the steps following analysis to diagnosis. The method provides the next course of action necessary in determining the deficiency or elevation of a particular fragment directly proportional to a concentration of a metabolite that may cause a genetic defect. In accordance with U.S. application Ser. No. 09/277,119, when an abnormal sample is flagged after being scanned, a recommended action is to be taken. The present method is a guideline for the necessary action following the preliminary analysis.

Internal standards are used to provide the quantitative information needed to detect specific components. Use of proper ratios of respective ions enables the detection of many metabolites at one time. Each particular metabolite is produced as a fragment yielding a concentration within the spectrometer after being quantified and derivatized from a blood spot. Each metabolite concentration is compared to a flag concentration, which is a quality assurance indicator used to identify a proper sampling quantification and analysis, and which is a diagnostic limit in determining whether or not the concentration of the metabolite is significant. The flag is pre-determined based on a standard deviation from what a normal concentration of a particular metabolite should be. This concentration threshold, or flag, must be appropriated for each scan done and for each type of metabolite reviewed. The concentration values produced will be above or below this threshold flag, which allows for the determination of the next course of action, whether it be a re-analysis or the interpretation that the baby is normal.

As an example, medium chain acyl-CoA dehydrogenase (MCAD) deficiency could be a result of an increased concentration of octanoylcarnitine (Chace et al.). Deficiency in the activity of MCAD presents with a Reye-like syndrome, mild hypoglycemia, or sudden death. The present method provides for numerical guidelines for determining just how significant the elevation is at the time of birth, and what the next step in the screening process would be, such as a follow-up and confirmatory DNA test. In this manner, decision trees for interpreting the concentrations for amino acids and acylcarnitine/carnitines are presented, some of which, if properly diagnosed, can lead to treatment. Each of these potentially fatal blood elevations or deficiencies is compared against the quantified concentration thresholds to allow for immediate attention and action. The comparison with the threshold flags also is a determining factor for maintaining instrument quality and accuracy. This decision making process, coupled with the current method of screening newborns using electrospray tandem MS/MS, allows for a complete protocol for analyzing and diagnosing newborns with genetic disorders.

BRIEF DESCRIPTION OF THE DRAWINGS

FIG. 4 is the decision tree for the implementation of the method for propionyl carnitine FIG. 5 is the decision tree for the implementation of the method for isovaleryl carnitine.

FIG. 6 is the decision tree for the implementation of the method for methionine.

FIG. 7 is the decision tree for the implementation of the method for glutaryl carnitine.

FIG. 8 is the decision tree for the implementation of the method for phenylalanine.

FIG. 9 is the decision tree for the implementation of the method for leucine.

FIG. 10 is the decision tree for the implementation of the method for citrulline.

FIG. 11 is the decision tree for the implementation of the method for octanoyl carnitine.

FIG. 12 is the decision tree for the implementation of the method for myristoyl carnitine.

FIG. 13 is the decision tree for the implementation of the method for hydroxy-C5.

DETAILED DESCRIPTION OF THE PREFERRED EMBODIMENT

The method will now be described in detail in relation to a preferred embodiment and implementation thereof which is exemplary in nature and descriptively specific as disclosed. As is customary, it will be understood that no limitation of the scope of the invention is thereby intended. The invention encompasses such alterations and further modifications in the illustrated device, and such further applications of the principles of the invention illustrated herein, as would normally occur to persons skilled in the art to which the invention relates.

Figure 1:
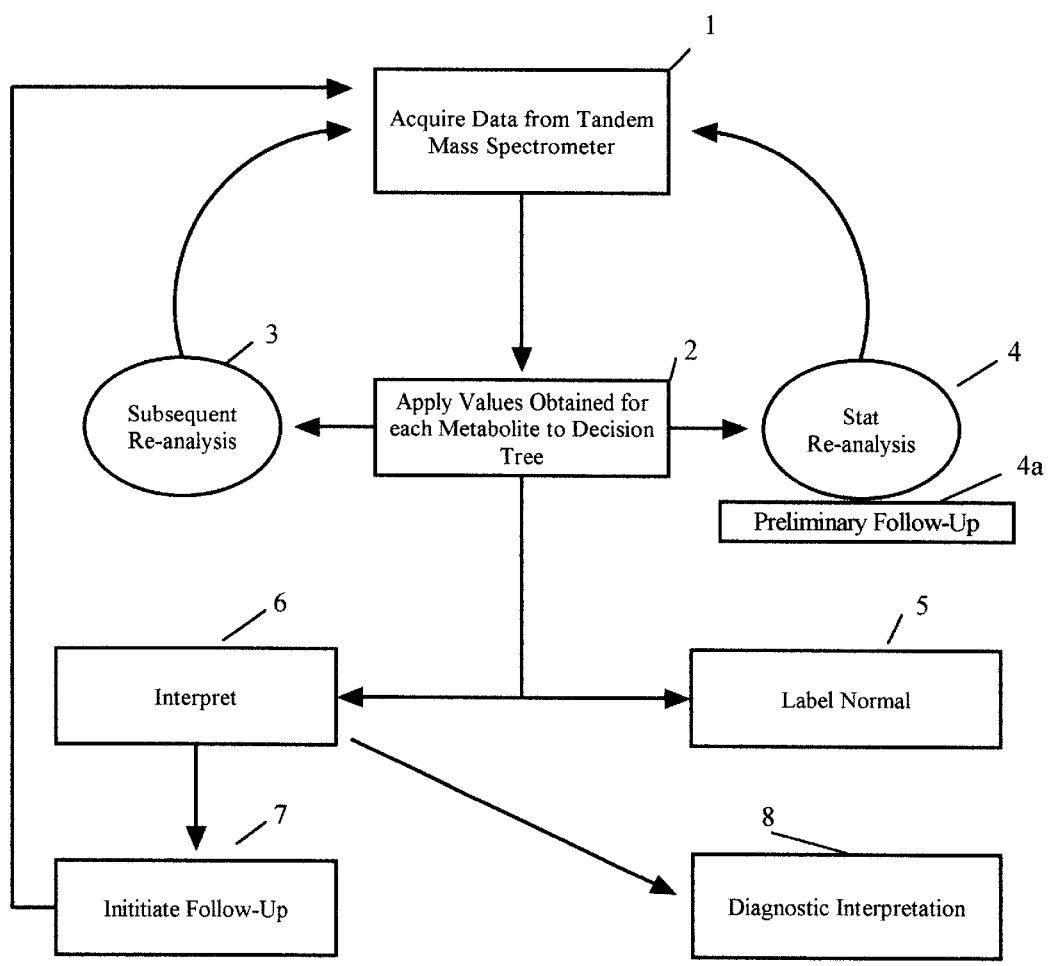
FIG. 1 is a flow diagram of the overall methodology representing the major steps involved from analysis to diagnosis.

The steps in the overall methodology are shown in FIG. 1. After the blood samples are scanned by the electrospray tandem mass spectrometer, the data is acquired 1. This data can be presented on a monitor to allow for viewing and/or printing of the output. As part of this data acquiring 1, the first values produced from the scan of the mass spectrometer are processed and printed into spreadsheet form to further allow checking of the calculations, a means of assuring accurate number production and quality. The acquired data 1 is then examined by applying the first values obtained to the decision tree 2 particular to a metabolite. The first values to be interpreted 2 consist of mean metabolite concentrations and molar ratio concentrations produced from the fragmentation of the metabolites scanned. The concentration of the particular metabolite is read from the fragmentation of the butyl ester occurring at a specific mass to charge value upon derivatization of the metabolite. This quantified number, normally in units of micromolarity, is compared to the flag threshold.

The metabolites, as further described, are grouped as carnitines/acylcarnitines or amino acids. Each particular metabolite is derivatized to enhance the detection of the fragment of concern, and would produce a peak upon scanning corresponding to a quantified concentration number, and compared to the decision tree 2 flag threshold, which is a particular standard deviation away from a mean value for the particular metabolite fragment concentration. The flag threshold particular for that metabolite is a diagnostic limit to these first values.

When the first values for the flags and metabolite fragment concentrations or molar ratio concentrations are applied to the decision tree 2, it is identified whether or not there needs to be a subsequent re-analysis 3, or an immediate, stat re-analysis 4. A subsequent analysis 3 may be necessarily performed if the scan revealed a mean concentration that is equal to or slightly greater than the pre-determined threshold for the flag setting. Each threshold is unique for a particular metabolite concentration, as further described. It should be understood that a concentration is deemed relevant if it exceeds a threshold when the metabolite may cause defects if elevated, and the concentration is relevant if it is below the threshold when the metabolite of question may cause defects if deficient. Because of this fact, any elevation or deficiency can be called a deviation. For the purposes of clarification, an elevation will be discussed, whereby a deficiency should be inherently understood depending on the metabolite. Both upper and lower concentration flag thresholds and molar ratio thresholds may be utilized in some cases where both an elevation and deficiency is significant in determining what defect may be present.

A stat re-analysis 4 may be performed if an initial concentration of the metabolite significantly deviates from the flag threshold, which may be evident of a genetic disorder. An immediate preliminary follow-up 4a would then follow. Whether or not the deviation is deemed significant depends on the amount by which the metabolite concentration deviates from the flag threshold based on the interpretation guide for each disorder. In any effect, a subsequent analysis 3 or a stat re-analysis 4 requires the data to be re-acquired 1. If the scan shows normal metabolite concentration levels as compared to the concentration flag thresholds and molar ratio thresholds, the interpretation may be that the blood component levels are normal 5.

Depending on which particular metabolite is being scanned, if the metabolite concentration is not significantly above the threshold, but still deviates in relation to the threshold, even after re-analysis, the next step would be to interpret 6 the sample as being evident of this elevation (or deficiency). In this case, a follow-up protocol 7 would be initiated, such that the detection process would be repeated and all attention would be focused on this sample. After any subsequent repeat, a diagnostic interpretation 8 may follow if the first concentration is consistent with any subsequent evaluation.

Figure 2:
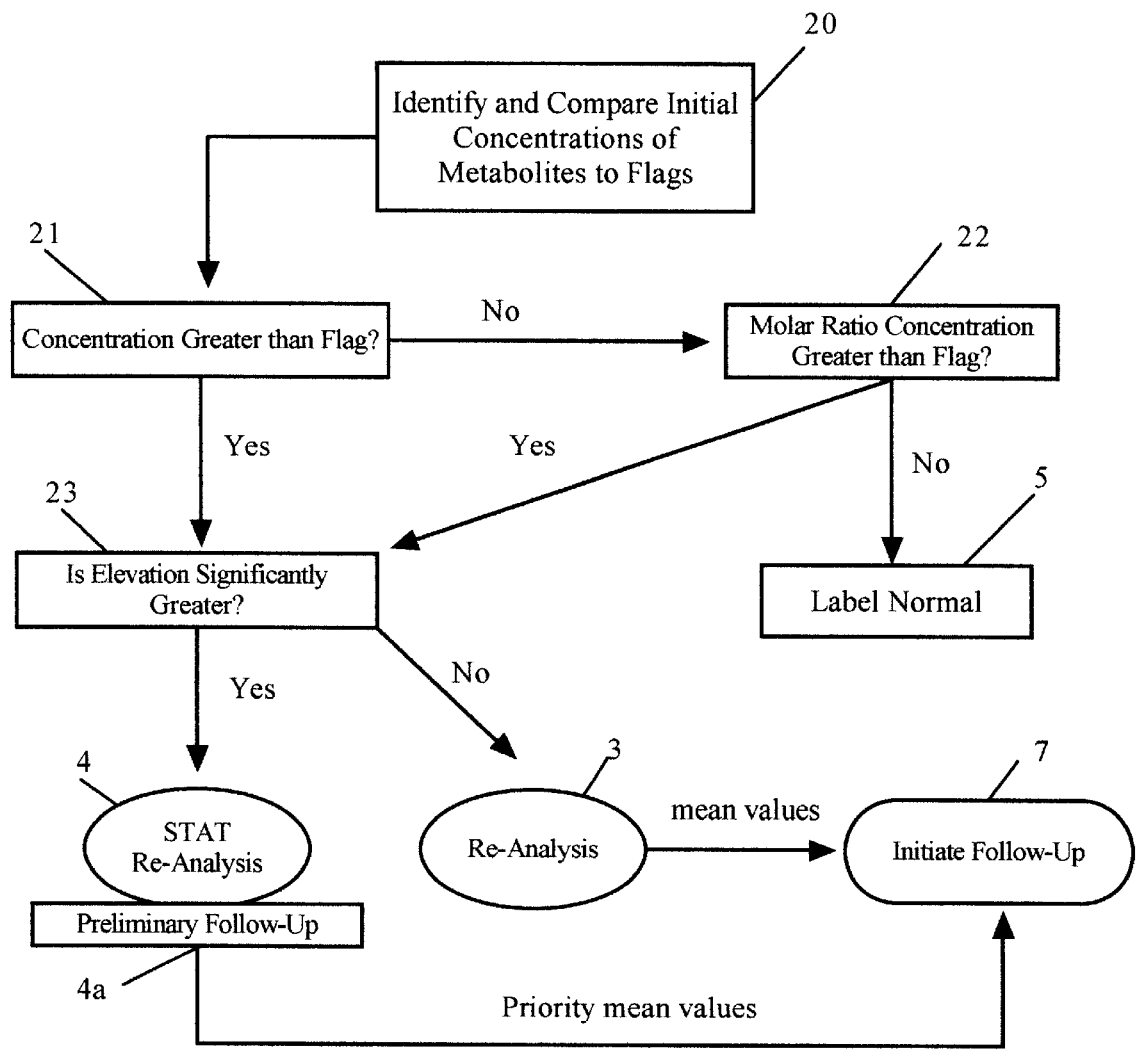
FIG. 2 is a flow diagram showing the more detailed steps and decision tree involved in the re-analysis protocol.

The criteria involved for deciding whether or not to subsequently re-analyze 3, or to immediately (stat) re-analyze 4 with an immediate preliminary follow-up 4a, are further described in relation to FIG. 2. The pre-determined threshold flags for each particular metabolite are compared to the initial concentrations of the metabolites 20 after being scanned. The threshold flag settings have been developed based upon many factors such as published reports, the clinical screening of individuals who are already sick, autopsy reports, and experience through repetition of genetic data analysis. If the initial concentration of the metabolite of interest is greater than the flag threshold 21, then a determination is made as to how significant the elevation is 23. This is determined by comparing each flag threshold to the initial concentration of the metabolite and identifying whether or not the elevation (or deficiency) exceeds the flag threshold by reference to criteria for each metabolite. If this were to occur, an immediate stat re-analysis 4 and preliminary follow-up 4a would be performed. This is achieved by prioritizing the sample to allow for an immediate preliminary follow-up and re-running the sample from the same filter card to acquire a set of prioritized values. These values are then averaged as a mean with the first values to form priority mean values because they are more significant for implementation into the follow-up protocol.

If the initial concentration of the metabolite is not greater than the flag threshold 21, the molar ratio concentrations are identified and compared to their respective concentration flag thresholds and molar ratio thresholds 22. The molar ratios are important because they account for variability of the blood spot on the filter card. Because the sample is originally dry, the variability of the thickness, number of cells, and change in volume must be accounted for. Thus, as the concentration of the metabolite may go up or down, the ratio of two analytes in one sample is a more sensitive indicator because they both change relative to one another.

If the molar ratio concentrations are not greater than the concentration flag thresholds and molar ratio thresholds 22, then the sample may be labeled as normal. However, if the molar ratio concentrations are found to be greater 22 by reference to the criteria particular for that metabolite, the elevation significance is then compared as above 23. Thus, if either the initial concentration of the metabolite or the molar ratios are significantly elevated by reference to the criteria, an immediate stat re-analysis 4 with preliminary follow-up 4a is performed. And in both cases, if the elevation is present by comparison to the flag threshold 21 but not significant 23, a sub-sequent re-analysis 3 is performed. This is achieved by acquiring a new set of data to obtain second values from the sample, by re-testing the sample and averaging the results to form mean values of the concentrations, which can then be implemented into the follow-up protocol, as follows.

A follow-up protocol is then initiated 7 following any re-analysis for determining any possible interpretation for diagnosis.

Figure 3:
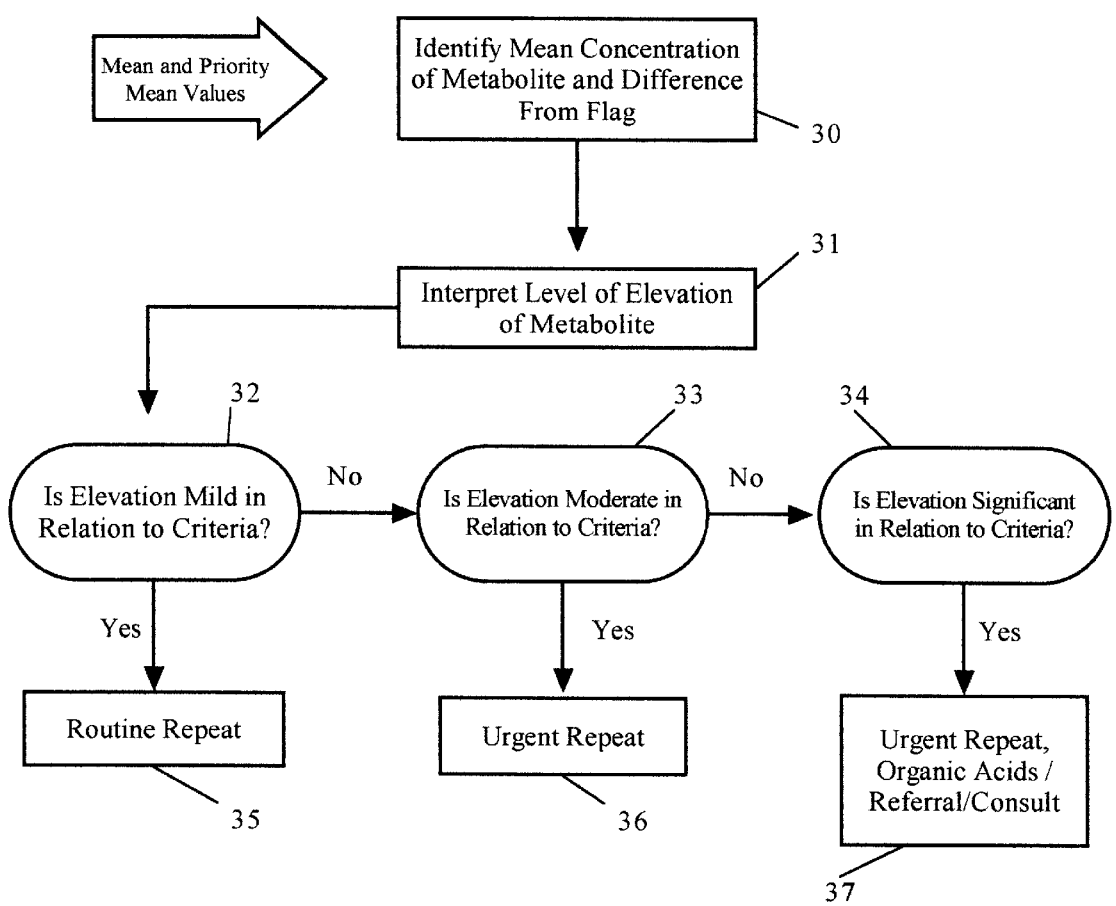
FIG. 3 is a flow diagram showing the more detailed steps and decision tree involved in the follow-up protocol.

FIG. 3 lays out the criteria for broadly initiating a follow-up 7. Any mean values or priority mean values are identified from the subsequent re-analysis 3 or the immediate re-analysis 4, respectively. These values that are elevated to some degree (dependent on decision matrix) above the flag threshold are identified 30. This follow-up 7 may also follow any re-analysis. The level of elevation (or deficiency, if required) is interpreted 31 as being mild 32, moderate 33, or significant 34 based on the criteria in the interpretation guide for each metabolite, as further described. If the elevation is considered mild 32 based on the difference from the threshold, a routine repeat 35 is performed. This involves performing a less prioritized repeat of the testing without an alert to a parent or physician.

If the elevation is considered moderate 33 based on the criteria, an urgent repeat 36 is performed, which is different from a routine repeat because the elevation is reported to a physician. Accordingly, the physician can suggest to see the baby and possibly get another sample or confirm the results.

If the elevation is considered significant 34 based on the criteria, an urgent repeat plus additional testing to obtain a third set of values, such as for propionic acidemia, or other organic acidemias, is performed along with a referral to a specialist particular to a disorder to ascertains an expertise for clinical evaluation.

The present method can be further understood by referencing the tables and criteria in FIGS. 4–10. Each figure represents the decision tree presented for each particular metabolite, which is necessary because each metabolite ionizes a butyl ester fragment at a different mass to charge (m/z) value, and each metabolite concentration (in units micromolarity [uM]) must be compared to a different threshold flag. The butyl ester fragment is directly proportional to the concentration of the metabolite. The preferred values of the threshold flags, or automated interpretation flag settings, are seen in tabulated form for each metabolite.

FIG. 4 is used in the method for assisting in the diagnosis of propionic acidemia after a dry blood spot on filter paper is derivatized and scanned using a tandem mass spectrometer. The method as previously discussed is applied using the flag thresholds 40 for all concentrations and molar ratios used for determining the level of elevation of propionyl carnitine. The flag thresholds 40 are preferably set at about 5.0 uM for the propionyl carnitine (C3) concentration, about 0.3 for the mrm scan of propionyl carnitine with acetyl carnitine (C3mrm/C2), and about 1.75 for the molar ratio of the propionyl carnitine with palmitoyl carnitine (C3/C16).

The criteria for re-analysis 41 and criteria for an immediate, or STAT re-analysis 42 in relation to the flag thresholds 40 are also shown. A subsequent re-analysis to obtain mean values is performed provided any of the following occurs:
i. C3 is equal to or greater than the C3 flag threshold;
ii. C3/C16 is greater than or equal to the C3/C16 flag threshold and C3/C2 is greater than the C3/C2 flag threshold and C3 is greater than about 2.5 uM;
iii. C3 is greater than about 4 uM, and either said C3/C16 is greater than said C3/C16 flag threshold or said C3/C2 is greater than said C3/C2 flag threshold.

An immediate, or STAT re-analysis with a preliminary follow-up to obtain priority mean values is performed provided any of the following occurs:
i. C3 is greater than about 9.0 uM;
ii C3 is greater than about 7.0 uM and the C3/C2 is greater than the C3/C2 flag threshold, or the C3/C16 is greater than the C3/C16 flag threshold.

The procedure is repeated to get mean values for implementation into a specific follow-up protocol 43, which ultimately leads to the diagnostic assistance for propionic acidemia.

FIG. 5 is used in the method for assisting in the diagnosis of isovaleric acidemia after a dry blood spot on filter paper is derivatized and scanned using a tandem mass spectrometer. The method as previously discussed is applied using the flag threshold 50 for the concentration used for determining the level of elevation of isovaleryl carnitine. The flag threshold 50 for isovaleryl carnitine is preferably set at about 0.8 uM.

Criteria for re-analysis 51 and criteria for an immediate, or STAT re-analysis 52 in relation to the flag threshold 50 for isovaleryl carnitine (C5) are also shown. A subsequent re-analysis 51 to obtain a mean value of C5 is performed provided the isovaleryl carnitine concentration (C5) is greater than or equal to the C5 flag threshold 50.

An immediate re-analysis 52 with a preliminary follow-up to obtain a priority mean value of an isovaleryl carnitine concentration (C5) is performed provided any of the following occurs:
i. the C5 is greater than about 2.0 uM;
ii. the C5 is greater than about 1.0 uM and the propionyl carnitine concentration (C3) [FIG. 4] is greater than about 2.5 uM.

The procedure is repeated to get mean values for implementation into a specific follow-up protocol 53, which ultimately leads to the diagnostic assistance for isovaleric acidemia.

FIG. 6 is used in the method for assisting in the diagnosis of hypermethionemia after a dry blood spot on filter paper is derivatized and scanned using a tandem mass spectrometer. The method as previously discussed is applied using the flag thresholds 60 for all concentrations and molar ratios used for determining the level of elevation of methionine. The flag thresholds 60 are preferably set at 60 uM for the methionine concentration (met) and 1 for the molar ratio of methionine and phenylalanine (met/phe).

The criteria for re-analysis 61 and criteria for an immediate, or STAT re-analysis 62 in relation to the flag thresholds are also shown. A subsequent re-analysis to obtain mean values is performed provided any of the following occur:

i. met is greater than the met flag threshold;

ii. met is greater than about 50 uM and the met/phe is greater than the met/phe flag threshold.

An immediate re-analysis with a preliminary follow-up to obtain priority mean values is performed provided any of the following occur:

i. met is greater than about 150 uM;

ii. met is greater than about 125 uM and the met/phe is greater than about 1.25.

The procedure is repeated to get mean values as previously discussed for implementation into a specific follow-up protocol 63, which ultimately leads to the diagnostic assistance for hypermethionemia.

FIG. 7 is used in the method for assisting in the diagnosis of glutaric acidemia after a dry. blood spot on filter paper is derivatized and scanned using a tandem mass spectrometer. The method as previously discussed is applied using the flag thresholds 70 for all concentrations and molar ratios used for determining the level of elevation of glutaryl carnitine. The flag thresholds 70 are preferably set at 0.17 uM for the glutaryl carnitine concentration (C5DC) and 0.12 for the molar ratio of glutaryl carnitine with palmitoyl carnitine (C5DC:C16).

Criteria for re-analysis 71 and criteria for an immediate, or STAT reanalysis 72 in relation to the flag thresholds are also shown. A subsequent re-analysis 71 to obtain mean values is performed provided any of the following occur:

i. C5DC is greater than the C5DC flag threshold;

ii. C5DC:C16 is greater than the C5DC:C16 flag threshold, and the C5DC is greater than about 0.14 uM.

An immediate re-analysis 72 with a preliminary follow-up to obtain priority mean values is performed provided any of the following occur:

i. C5DC is greater than about 0.4 uM;

ii. C5DC is greater than about 0.2 uM, and the C5DC:C16 is greater than about 0.2 uM.

The procedure is repeated to get mean values as previously discussed for implementation into a specific follow-up protocol 73, which ultimately leads to the diagnostic assistance for glutaric acidemia.

FIG. 8 is used in the method for assisting in the diagnosis of phenylketonuria (PKU) after. a dry blood spot on filter paper is derivatized and scanned using a tandem mass spectrometer. The method as previously discussed is applied using the flag thresholds 80 for all concentrations and molar ratios used for determining the level of elevation of phenylalanine (phe) or tyrosine (tyr). The flag thresholds 80 are preferably set at 130 uM for the phenylalanine concentration (phe), 350 uM for the tyrosine concentration (tyr), and 2.5 for the molar ratio of phehylalanine with tyrosine (phe/tyr).

The criteria for re-analysis 81 and criteria for an immediate, or STAT re-analysis 82 in relation to the flag thresholds are also shown. A subsequent re-analysis 81 to obtain mean values is performed provided any of the following occur:

i. phe is greater than the phe flag threshold;

ii. tyr is greater than the tyr flag threshold;

iii. phe/tyr is greater than the phe/tyr flag threshold and the phe is greater than about 100 uM.

An immediate re-analysis 82 with a preliminary follow-up to obtain priority mean values is performed provided any of the following occur:

i. phe is greater than about 240 uM;

ii. phe is greater than about 180 uM and the phe/tyr is greater than the phe/tyr flag threshold.

The procedure is repeated to get mean values as previously discussed for implementation into a specific follow-up protocol 83, which ultimately leads to the diagnostic assistance for PKU.

FIG. 9 is used in the method for assisting in the diagnosis of Maple Syrup Urine Disease (MSUD) after a dry blood spot on filter paper is derivatized and scanned using a tandem mass spectrometer. The method as previously discussed is applied using the flag thresholds 90 for all concentrations and molar ratios used for determining the level of elevation of leucine. The flag thresholds are preferably set at 325 uM for the concentration of a combination of leucine and isoleucine (leu+Ile); 300 uM for a concentration of valine (val); 8.0 for the molar ratio of leucine with phenylalanine (leu/phe); and 2.25 for the molar ratio of leucine with alanine (leu/ala).

The criteria for re-analysis 91 and criteria for an immediate, or STAT re-analysis 92 in relation to the flag thresholds are also shown. A subsequent re-analysis 91 to obtain mean values is performed provided any of the following occur:

i. leu+ile is greater than about 400 uM;

ii. leu+ile is greater than about 350 uM and val is greater than the val flag threshold;

iii. leu+ile is greater than the leu+ile flag threshold and the leu/ala is greater than the leu/ala flag threshold, or the leu/phe is greater than the leu/phe flag threshold and the val is greater than the val flag threshold;

An immediate re-analysis 92 with a preliminary follow-up to obtain priority mean values is performed provided any of the following occur:

i. leu+ile is greater than about 500 uM;

ii. leu+ile is greater than about 400 uM and the leu/phe is greater than the leu/phe flag threshold and the leu/ala is greater than the leu/ala flag threshold.

The procedure is repeated to get mean values as previously discussed for implementation into a specific follow-up protocol 93, which ultimately leads to the diagnostic assistance for MSUD.

FIG. 10 is used in the method for assisting in the diagnosis of citrullinemia after a dry blood spot on filter paper is derivatized and scanned using a tandem mass spectrometer. The method as previously discussed is applied using the flag threshold 100 for the concentrations used for determining the level of elevation of citrulline. The flag threshold 100 is preferably set at 55 uM for a concentration of citrulline determined after a full scan (cit), and 55 uM for a concentration of citrulline determined after an mrm scan (cit [mrm]).

The criteria for re-analysis 101 and criteria for an immediate, or STAT re-analysis 102 in relation to the flag thresholds are also shown. A subsequent re-analysis 101 to obtain mean values is performed provided the following occurs:

i. cit or cit(mrm) is greater than the cit flag threshold or the cit(mrm) flag threshold.

An immediate re-analysis 102 with a preliminary follow-up to obtain priority mean values is performed provided the following occurs:

i. cit is greater than about 100 uM.

The procedure is repeated to get mean values as previously discussed for implementation into a specific follow-up protocol 103, which ultimately leads to the diagnostic assistance for citrullinemia.

FIG. 11 is used in the method for assisting in the diagnosis of medium-chain acylcoenzyme A dehydrogenase (MCAD) deficiency after a dry blood spot on filter paper is derivatized and scanned using a tandem mass spectrometer. The method as previously discussed is applied using the flag thresholds 110 for all concentrations and molar ratios used for determining the level of elevation of octanoyl carnitine. The flag thresholds 110 are preferably set at 0.35 uM for an octanoyl carnitine concentration (C8); 0.28 for a molar ratio of octanoyl carnitine with palmitoyl carnitine; 0.16 uM for a hexanoyl carnitine concentration (C6); 0.32 uM for a decenoyl carnitine concentration (C10:1); and 0.42 uM for a decanoyl carnitine concentration (C10).

The criteria for re-analysis 111 and criteria for an immediate, or STAT re-analysis 112 in relation to the flag thresholds 110 are also shown. A subsequent re-analysis 111 to obtain mean values is performed provided any of the following occur:

i. C8 is greater than or equal-to about 0.4 uM;
ii. C8 is greater than about 0.3 uM and the C8/C16 is greater than about 0.15;
iii. C8 is greater than about 0.3 uM and the C6 is greater than about 0.2 uM, or the C10:1 is greater than about 0.2 uM and the C10 is greater than about 0.3 uM with a low acetyl flag;

An immediate re-analysis 112 with a preliminary follow-up to obtain priority mean values is performed provided any of the following occur:

i. C8 is greater than about 1.0 uM;
ii. C8 is greater than about 0.5 uM and the C8/C16 is greater than about 0.35, or the C6 is greater than about 0.3 uM and the C10:1 is greater than about 0.3 uM.

The procedure is repeated to get mean values as previously discussed for implementation into a specific follow-up protocol 113, which ultimately leads to the diagnostic assistance for MCAD deficiency.

FIG. 12 is used in the method for assisting in the diagnosis of very long chain acylCoA dehydrogenase (VLCAD) deficiency after a dry blood spot on filter paper is derivatized and scanned using a tandem mass spectrometer. The method as previously discussed is applied using the flag thresholds 120 for all concentrations and molar ratios used for determining the level of elevation of the myristoylcarnitines. The flag thresholds 120 are preferably set at 0.85 uM for a saturated myristoyl carnitine concentration (C14); 0.70 for an unsaturated myristoyl carnitine concentration (C14:1); and 0.24 for a molar ratio of the unsaturated (C14:1) with palmitoyl carnitine.

The criteria for re-analysis 121 and criteria for an immediate, or STAT re-analysis 122 in relation to the flag thresholds are also shown. A subsequent re-analysis 121 to obtain mean values is performed provided any of the following occur:

i. C14 is greater than the C14 flag threshold, or said C14:1 is greater than the C14:1 flag threshold;
ii. C14 is greater than about 0.75 uM, or the C14:1 is greater than about 0.65 uM and the C14:1/C16 is greater than about 0.24.

An immediate re-analysis 122 with a preliminary follow-up to obtain priority mean values is performed provided any of the following occur:

i. C14 is greater than about 2.0 uM, or the C14:1 is greater than about 1.5 uM;
ii. C14 is greater than about 1.5 uM, and the C14:1 is greater than about 1.0 uM, and the C14:1/C16 is greater than about 0.3.

The procedure is repeated to get mean values as previously discussed for implementation into a specific follow-up protocol 123, which ultimately leads to the diagnostic assistance for VLCAD deficiency.

FIG. 13 is used in the method for assisting in the diagnosis of crotonyl co-A carboxylase deficiency after a dry blood spot on filter paper is derivatized and scanned using a tandem mass 1s spectrometer. The method as previously discussed is applied using the flag thresholds 130 for all concentrations used for determining the level of elevation of the hydroxy C5. The flag thresholds 130 are preferably set at 0.85 uM for a hydroxy-C5 concentration (C5 OH), and 0.35for a C5:1 concentration.

The criteria for re-analysis 131 and criteria for an immediate, or STAT re-analysis 132 in relation to the flag thresholds are also shown. A subsequent re-analysis 131 to obtain mean values is performed provided any of the following occur:

i. C5OH is greater than or equal to the C5OH flag threshold;
ii. C5:1 is greater than or equal to the C5:1 flag threshold;

An immediate re-analysis 132 with a preliminary follow-up to obtain priority mean values is performed provided any of the following occur:

i. C5OH is greater than about 3.0 uM;
ii. C5:1 is greater than about 1.0 uM.

The procedure is repeated to get mean values as previously discussed for implementation into a specific follow-up protocol 133, which ultimately leads to the diagnostic assistance for crotonyl coA carboxylase deficiency.

C5OH represents a hydroxy-C5, which is an abbreviated form for hydroxyisovalerylcarnitine and/or hydroyxlmethylbutylcarnitine. The C5:1 is the unsaturated form known as tiglylcarnitine.

In conclusion, according to each decision tree, or interpretation guide particular for each metabolite, the present method allows the data that is acquired to be quantified and reported to a physician to assist in a diagnosis of a genetic disease resulting from the deviation (elevation or deficiency) of a blood metabolite. The method allows one to provide information to a physician that additional tests and/or clinical assessments (check up, examination, etc) are necessary because of the resulting elevation or deficiency of the metabolite, which then results in the confirmed final diagnosis. The values of the flag thresholds for a particular concentration and the molar ratio flag thresholds must be quantified for a consistent and accurate interpretation of acylcarnitine and amino acid data.

TERMS

It should be understood that "about" as used in relation to FIGS. 4–13 means±15% of the value shown in the criteria for each figure, which values are dependent upon the flag threshold. Any change in the value of the flag threshold, which might result from filter paper characteristics, new insights into disease characteristics, new diseases found, methods of sample collection, changes in methodology, or corrections from quality assurance programs, would necessitate the relative change of each value in the criteria for all follow-ups. Thus, all values shown in the drawings are the preferred values, which might fluctuate then by no more than±15%.

I claim:

1. A method for assisting in a diagnosis of propionic acidemia by interpreting data produced after a dry blood spot on filter paper is derivatized and scanned by a tandem mass spectrometer, comprising the steps of:

acquiring said data, wherein said data includes values comprised of a propionyl carnitine concentration (C3), a molar ratio of an mrm scan of propionyl carnitine and acetyl carnitine (C3mrm/C2), and a molar ratio of propionyl carnitine and palmitoyl carnitine (C3/C16);

applying said values to a propionyl carnitine (C3) decision tree, wherein said decision tree further comprises a C3 flag threshold, a C3mrm/C2 flag threshold, and a C3/C16 flag threshold as diagnostic limits to said C3, said C3mrm/C2, and said C3/C16 respectively;

comparing said values, respectively, with each of said flag thresholds;

identifying whether or not there is an elevation of any of said values above any of said flag thresholds;

interpreting said sample as being normal for said propionyl carnitine, provided there is no said elevation of any of said values;

performing a subsequent re-analysis to obtain mean values, provided any of the following occurs:
  i. said C3 is equal to or greater than said C3 flag threshold;
  ii. said C3/C16 is greater than or equal to said C3/C16 flag threshold and said C3/C2 is greater than said C3/C2 flag threshold and said C3 is greater than about 2.5 uM;
  iii. said C3 is greater than about 4 uM, and either said C3/C16 is greater than said C3/C16 flag threshold or said C3/C2 is greater than said C3/C2 flag threshold;

performing an immediate re-analysis with a preliminary follow-up to obtain priority mean values, provided any of the following occurs:
  i. said C3 is greater than about 9.0 uM;
  ii. said C3 is greater than about 7.0 uM and said C3/C2 is greater than said C3/C2 flag threshold or said C3/C16 is greater than said C3/C16 flag threshold; and, initiating a follow-up protocol based on follow-up criteria utilizing said mean values or said priority mean values for diagnostic purposes provided either said subsequent re-analysis or said immediate re-analysis is performed;

reporting said data to a physician to assist in said diagnosis of propionic acidemia.

2. The method of claim 1, wherein said C3 flag threshold, said C3mrm/C2 flag threshold, and said C3/C16 flag threshold are, respectively, 5.0 uM, 0.3 uM, and 1.75.

3. A method for assisting in a diagnosis of isovaleric acidemia by interpreting data produced after a dry blood spot on filter paper is derivatized and scanned by a tandem mass spectrometer, comprising the steps of:

acquiring said data, wherein said data includes values comprised of an isovaleryl carnitine concentration (C5) and a propionyl carnitine concentration (C3);

applying said isovaleryl carnitine concentration (C5) to an isovaleryl carnitine (C5) decision tree, wherein said decision tree further comprises a C5 flag threshold as diagnostic limit to said isovaleryl carnitine concentration (C5);

comparing said C5 to said flag threshold;

identifying whether or not there is an elevation of C5 above said flag threshold;

interpreting said sample as being normal for said isovaleryl carnitine, provided there is no said elevation of said C5;

performing a subsequent re-analysis to obtain a mean value of said C5, provided said C5 is greater than or equal to said C5 flag threshold;

performing an immediate re-analysis with a preliminary follow-up to obtain a priority mean value of said C5, provided any of the following occurs:
  i. said C5 is greater than about 2.0 uM;
  ii. said C5 is greater than about 1.0 uM and said C3 is greater than about 2.5 uM;

initiating a follow-up protocol based on follow up criteria utilizing said-mean value or said priority mean value for diagnostic purposes provided either said subsequent re-analysis or said immediate re-analysis is performed; and, reporting said data to a physician to assist in said diagnosis of isovaleric acidemia.

4. The method of claim 3, wherein said C5 flag threshold is 0.8 uM.

5. A method for assisting in a diagnosis of hypermethionemia by interpreting data produced after a dry blood spot on filter paper is derivatized and scanned by a tandem mass spectrometer, comprising the steps of:

acquiring said data, wherein said data includes values consisting essentially of a methionine concentration (met) and a molar ratio of methionine and phenylalanine (met/phe);

applying said values to a methionine (met) decision tree, wherein said decision tree further comprises a methionine flag threshold and a met/phe flag threshold as a diagnostic limit to said methionine concentration (met);

comparing said values, respectively, to each said flag threshold;

identifying whether or not there is an elevation of any of said values above any of said flag thresholds;

interpreting said sample as being normal for said hypermethionemia, provided there is no said elevation of any of said values;

performing a subsequent re-analysis to obtain mean values, provided any of the following occur:
  i. said met is greater than said met flag threshold;
  ii. said met is greater than about 50 uM and said met/phe is greater than said met/phe flag threshold;

performing an immediate re-analysis with a preliminary follow-up to obtain priority mean values, provided any of the following occur:
  i. said met is greater than about 150 uM;
  ii. said met is greater than about 125 uM and said met/phe is greater than about 1.25;

initiating a follow-up protocol based on follow-up criteria utilizing said mean values or said priority mean values for diagnostic purposes provided either said subsequent re-analysis or said immediate re-analysis is performed; and, reporting said data to a physician to assist in said diagnosis of hypermethionemia.

6. The method of claim 5, wherein said methionine flag threshold and said met/phe flag threshold are, respectively, 60 uM and 1.0.

7. A method for assisting in a diagnosis of glutaric acidemia by interpreting data produced after a dry blood spot on filter paper is derivatized and scanned by a tandem mass spectrometer, comprising the steps of:

acquiring said data, wherein said data includes values comprised of a glutaryl carnitine concentration (C5DC) and a molar ratio of glutaryl carnitine and palmitoyl carnitine (C5DC:C16);

applying said values to a glutaryl carnitine (C5DC) decision tree, wherein said decision tree further comprises a C5DC flag threshold and a C5DC:C16 flag threshold as diagnostic limits to said glutaryl carnitine concentration (C5DC) and said C5DC:C16 respectively;

comparing said values, respectively, to each of said flag thresholds;

identifying whether or not there is an elevation of any of said values above any of said flag thresholds;

interpreting said sample as being normal for said glutaric acidemia, provided there is no said elevation of any of said values;

performing a subsequent re-analysis to obtain mean values, provided any of the following occur:
  i. said C5DC is greater than said C5DC flag threshold;
  ii. said C5DC:C16 is greater than said C5DC:C16 flag threshold and said C5DC is greater than about 0.14 uM;

performing an immediate re-analysis with a preliminary follow-up to obtain priority mean values, provided any of the following occur:
  i. said C5DC is greater than about 0.4 uM;
  ii. said C5DC is greater than about 0.2 uM and said C5DC:C16 is greater than about 0.2 uM;

initiating a follow-up protocol based on follow up criteria utilizing said mean values or said priority mean values for diagnostic purposes provided either said subsequent re-analysis or said immediate re-analysis is performed; and, reporting said data to a physician to assist in said diagnosis of glutaric acidemia.

8. The method of claim 7, wherein said C5DC flag threshold and said C5DC:C16 flag threshold are, respectively, 0.17 uM and 0.12.

9. A method for assisting in a diagnosis of phenylketonuria by interpreting data produced after a dry blood spot on filter paper is derivatized and scanned by a tandem mass spectrometer, comprising the steps of:

acquiring said data, wherein said data includes values consisting essentially of a phenylalanine concentration (phe), a tyrosine concentration (tyr), and a molar ratio of phenylalanine and tyrosine (phe/tyr);

applying said values to a phenylalanine (phe) decision tree, wherein said decision tree further comprises a phe flag threshold, a tyr flag threshold, and a phe/tyr flag threshold as diagnostic limits to said phe, said tyr, and said phe/tyr molar ratio respectively;

comparing said values, respectively, to each of said flag thresholds;

identifying whether or not there is an elevation of any of said values above any of said flag thresholds;

interpreting said sample as being normal for said phenylketonuria, provided there is no said elevation of any of said values;

performing a subsequent re-analysis to obtain mean values, provided any of the following occur:
  i. said phe is greater than said phe flag threshold;
  ii. said tyr is greater than said tyr flag threshold;
  iii. said phe/tyr is greater than said phe/tyr flag threshold and said phe is greater than 100 uM;

performing an immediate re-analysis with a preliminary follow-up to obtain priority mean values, provided any of the following occur:
  i. said phe is greater than about 240 uM;
  ii. said phe is greater than about 180 uM and said phe/tyr is greater than said phe/tyr flag threshold;

initiating a follow-up protocol based on follow-up criteria utilizing said mean values or said priority mean values for diagnostic purposes provided either said subsequent re-analysis or said immediate re-analysis is performed; and, reporting said data to a physician to assist in said diagnosis of phenylketonuria.

10. The method of claim 9, wherein said phe flag threshold, said tyr flag threshold, and said phe/tyr flag threshold are, respectively, 130 uM, 350 uM, and 2.5.

11. A method for assisting in a diagnosis of Maple Syrup Urine Disease (MSUD) by interpreting data produced after a dry blood spot on filter paper is derivatized and scanned by a tandem mass spectrometer, comprising the steps of:

acquiring said data, wherein said data includes values comprised of a leucine+isoleucine concentration (leu+ile), a valine concentration (val), a molar ratio of leucine and phenylalanine (leu/phe), and a molar ratio of leucine and alanine (leu/ala).

applying said values to a leucine (leu) decision tree, wherein said decision tree further comprises a leu+ile flag threshold, a val flag threshold, a leu/phe molar ratio flag threshold, and a leu/ala molar ratio flag threshold as diagnostic limits to said leu+ile, said val, said leu/phe, and said leu/ala respectively;

comparing said values, respectively, to each of said flag thresholds;

identifying whether or not there is an elevation of any of said values above any of said flag thresholds;

interpreting said sample as being normal for said MSUD, provided there is no said elevation of any of said values;

performing a subsequent re-analysis to obtain mean values, provided any of the following occur:
  i. said leu+ile is greater than about 400 uM;
  ii. said leu+ile is greater than about 350 uM and said val is greater than said val flag threshold;
  iii. said leu+ile is greater than said leu+ile flag threshold and said leu/ala is greater than said leu/ala flag threshold, or said leu/phe is greater than said leu/phe flag threshold and said val is greater than said val flag threshold;

performing an immediate re-analysis with a preliminary follow-up to obtain priority mean values, provided any of the following occur:
  i. said leu+ile is greater than about 500 uM;
  ii. said leu+ile is greater than about 400 uM and said leu/phe is greater than said leu/phe flag threshold and said leu/ala is greater than said leu/ala flag threshold;

initiating a follow-up protocol based on follow-up criteria utilizing said mean values or said priority mean values for diagnostic purposes provided either said subsequent re-analysis or said immediate re-analysis is performed; and, reporting said data to a physician to assist in said diagnosis of MSUD.

12. The method claim 11, wherein said leu+ile flag threshold, said val flag threshold, said leu/phe flag threshold, and said leu/ala flag threshold are, respectively, 325 uM, 300 uM, 8.0, and 2.25.

13. A method for assisting in a diagnosis of citrullinemia by interpreting data produced after a dry blood spot on filter paper is derivatized and scanned by a tandem mass spectrometer, comprising the steps of:
  acquiring said data, wherein said data includes values comprised of a citrulline concentration (cit) and a citrulline concentration after an mrm scan (cit[mrm]);
  applying said values to a citrulline (cit) decision tree, wherein said decision tree further comprises a cit flag threshold and a cit(mrm) flag threshold as diagnostic limits to said citrulline concentration (cit) and said cit(mrm) concentration respectively;
  comparing said values, respectively, to each of said flag thresholds;
  identifying whether or not there is an elevation of any of said values above any of said flag thresholds;
  interpreting said sample as being normal for said citrullinemia, provided there is no said elevation of any of said values;
  performing a subsequent re-analysis to obtain mean values, provided any of the following occur:
    i. said cit or said cit(mrm) is greater than said cit flag threshold or said cit(mrm) flag threshold;
  performing an immediate re-analysis with a preliminary follow-up to obtain priority mean values, provided any of the following occur:
    i. said cit is greater than about 100 uM;
  initiating a follow-up protocol based on follow up criteria utilizing said mean values or said priority mean values for diagnostic purposes provided either said subsequent re-analysis or said immediate re-analysis is performed; and,
  reporting said data to a physician to assist in said diagnosis of citrullinemia.

14. The method of claim 13, wherein said cit flag threshold and said cit(mrm) flag threshold are both 55 uM.

15. A method for assisting in a diagnosis of medium-chain acyl-coenzyme A dehydrogenase (MCAD) deficiency by interpreting data produced after a dry blood spot on filter paper is derivatized and scanned by a tandem mass spectrometer, comprising the steps of:
  acquiring said data, wherein said data includes values comprised of an octanoyl carnitine concentration (C8), a molar ratio of octanoyl carnitine and palmitoyl carnitine (C8/C16), a hexanoyl carnitine concentration (C6), a decenoyl carnitine concentration (C10:1), and a decanoyl carnitine concentration (C10);
  applying said values to an octanoyl carnitine (C8) decision tree, wherein said decision tree further comprises a C8 flag threshold, a C8/C16 molar ratio flag threshold, a C6 flag threshold, a C10:1 flag threshold, and a C10 flag threshold as diagnostic limits to said C8, said C8/C16, said C6, said C10:1, and said C10 respectively;
  comparing said values, respectively, to each of said flag thresholds;
  identifying whether or not there is an elevation of any of said values above any of said flag thresholds;
  interpreting said sample as being normal for said MCAD deficiency, provided there is no said elevation of any of said values;
  performing a subsequent re-analysis to obtain mean values, provided any of the following occur:
    i. said C8 is greater than or equal to about 0.4 uM;
    ii. said C8 is greater than about 0.3 uM and said C8/C16 is greater than about 0.15;
    iii. said C8 is greater than about 0.3 uM and said C6 is greater than about 0.2 uM, or said C10:1 is greater than about 0.2 uM and said C10 is greater than about 0.3 uM with a low acetyl flag;
  performing an immediate re-analysis with a preliminary follow-up to obtain priority mean values, provided any of the following occur:
    i. said C8 is greater than about 1.0 uM;
    ii. said C8 is greater than about 0.5 uM and said C8/C16 is greater than about 0.35, or said C6 is greater than about 0.3 uM and said C10:1 is greater than about 0.3 uM;
  initiating a follow-up protocol based on follow-up criteria utilizing said mean values or said priority mean values for diagnostic purposes provided either said subsequent re-analysis or said immediate re-analysis is performed; and,
  reporting said data to a physician to assist in said diagnosis of MCAD deficiency.

16. The method of claim 15, wherein said C8 flag threshold, said C8/C16 flag threshold, said C6 flag threshold, said C10:1 flag threshold, and said C10 flag threshold are, respectively, 0.35 uM, 0.28, 0.16 uM, 0.32 uM, and 0.42 uM.

17. A method for assisting in a diagnosis of VLCAD deficiency by interpreting data produced after a dry blood spot on filter paper is derivatized and scanned by a tandem mass spectrometer, comprising the steps of:
  acquiring said data, wherein said data includes values comprised of a saturated myristoyl carnitine concentration (C14), an unsaturated myristoyl carnitine concentration (C14:1), and a molar ratio of C14:1 and palmitoyl carnitine (C16);
  applying said values to a myristoyl carnitine (C14) decision tree, wherein said decision tree further comprises a C14 flag threshold, a C14:1 flag threshold, and a C14:1/C16 flag threshold as diagnostic limits to said C14, said C14:1, and said C14:1/C16 respectively;
  comparing said values, respectively, to each of said flag thresholds;
  identifying whether or not there is an elevation of any of said values above any of said flag thresholds;
  interpreting said sample as being normal for said MSUD, provided there is no said elevation of any of said values;
  performing a subsequent re-analysis to obtain mean values, provided any of the following occur:
    i. said C14 is greater than said C14 flag threshold or said C14:1 is greater than said C14:1 flag threshold;
  said C14 is greater than about 0.75 uM or said C14:1 is greater than about 0.65 uM and said C14:1/C16 is greater than about 0.24;
  performing an immediate re-analysis with a preliminary follow-up to obtain priority mean values, provided any of the following occur:
    i. said C14 is greater than about 2.0 uM or said C14:1 is greater than about 1.5 uM;
    ii. said C14 is greater than about 1.5 uM and said C14:1 is greater than about 1.0 uM and said C14:1/C16 is greater than about 0.3;

initiating a follow-up protocol based on follow-up criteria utilizing said mean values or said priority mean values for diagnostic purposes provided either said subsequent re-analysis or said immediate re-analysis is performed; and, reporting said data to a physician to assist in said diagnosis of VLCAD deficiency.

18. The method of claim 17, wherein said C14 flag threshold, said C14:1 flag threshold, and said C14:1/C16 flag threshold are, respectively, 0.85 uM, 0.70 uM, and 0.24.

19. A method for assisting in a diagnosis of a Crotonyl co-A carboxylase deficiency elevation by interpreting data produced after a dry blood spot on filter paper is derivatized and scanned by a tandem mass spectrometer, comprising the steps of:

acquiring said data, wherein said data includes values comprised of a C5-OH and C5:1;

applying said values to a hydroxy-C5 (C5-OH) decision tree, wherein said decision tree further comprises a C5OH flag threshold and a C5:1 flag threshold as diagnostic limits to said C5OH and said C5:1 respectively;

comparing said values, respectively, to each of said flag thresholds;

identifying whether or not there is an elevation of any of said values above any of said flag thresholds;

interpreting said sample as being normal for said crotonyl co-A carboxylase deficiency, provided there is no said elevation of any of said values;

performing a subsequent re-analysis to obtain mean values, provided any of the following occur:
  said C5OH is greater than or equal to said C5OH flag threshold;
  said C5:1 is greater than or equal to said C5:1 flag threshold;

performing an immediate re-analysis with a preliminary follow-up to obtain priority mean values, provided any of the following occur:
  i. said C5OH is greater than about 3.0 uM;
  ii. said C5:1 is greater than about 1.0 uM;

initiating a follow-up protocol based on follow-up criteria utilizing said mean values or said priority mean values for diagnostic purposes provided either said subsequent re-analysis or said immediate re-analysis is performed; and, reporting said data to a physician to assist in said diagnosis of crotonyl co-A carboxylase deficiency.

20. The method of claim 19, wherein said C5OH flag threshold and said C5:1 flag threshold are, respectively, 0.85 uM and 0.35 uM.

* * * * *

Disclaimer

6,455,321 — Donald H. Chace, Pittsburgh, PA (US). METHOD FOR INTERPRETING TANDEM MASS SPECTROMETRY DATA FOR CLINICAL DIAGNOSIS. Patent dated Sept. 24, 2002. Disclaimer filed Nov. 8, 2004 by the Assignee, Neo Gen Screening, Inc.

Hereby enters this disclaimer to claims 9 and 10, of said patent.

*(Official Gazette May 10, 2005)*